United States Patent
Leitner

(10) Patent No.: US 7,753,921 B2
(45) Date of Patent: Jul. 13, 2010

(54) METHOD AND APPARATUS FOR DETERMINING THE POSITION OF AN OBJECT

(75) Inventor: François Leitner, Uriage (FR)

(73) Assignee: Aesculap AG, Tuttlingen (DE)

( * ) Notice: Subject to any disclaimer, the term of this patent is extended or adjusted under 35 U.S.C. 154(b) by 832 days.

(21) Appl. No.: 11/540,936

(22) Filed: Sep. 29, 2006

(65) Prior Publication Data

US 2007/0083133 A1    Apr. 12, 2007

(30) Foreign Application Priority Data

Oct. 6, 2005    (DE)    ........................ 10 2005 047 895

(51) Int. Cl.
*A61B 19/00* (2006.01)
(52) U.S. Cl. ...................................................... 606/130
(58) Field of Classification Search ................. 128/920; 600/407, 415, 417, 424–427, 429, 473, 492, 600/587, 595; 606/1, 64, 70, 79–88, 91, 606/96–99, 102, 104, 130
See application file for complete search history.

(56) References Cited

U.S. PATENT DOCUMENTS

| | | | | |
|---|---|---|---|---|
| 5,921,992 | A * | 7/1999 | Costales et al. | 606/130 |
| 6,223,067 | B1 * | 4/2001 | Vilsmeier et al. | 600/426 |
| 6,932,823 | B2 * | 8/2005 | Grimm et al. | 606/130 |
| 7,302,355 | B2 * | 11/2007 | Jansen et al. | 702/95 |
| 7,316,687 | B2 * | 1/2008 | Aikins et al. | 606/70 |
| 2004/0034313 | A1 | 2/2004 | Leitner | |
| 2004/0068179 | A1 * | 4/2004 | Jutras et al. | 600/424 |
| 2005/0015022 | A1 | 1/2005 | Richard et al. | |
| 2005/0215888 | A1 * | 9/2005 | Grimm et al. | 600/426 |
| 2006/0161059 | A1 * | 7/2006 | Wilson | 600/424 |
| 2009/0099445 | A1 * | 4/2009 | Burger | 600/424 |

FOREIGN PATENT DOCUMENTS

DE    100 62 580    7/2002

* cited by examiner

*Primary Examiner*—Todd E Manahan
*Assistant Examiner*—Richard Dault
(74) *Attorney, Agent, or Firm*—Lipsitz & McAllister, LLC

(57) ABSTRACT

Methods and apparatus for determining the orientation and the position of an object in space with the assistance of a sensing instrument are provided. The sensing instrument is provided with a marking element. The orientation and position of the marking element is determinable by means of the navigation system. In order to be able to carry out a reliable determination of the position, even under confined conditions of access, the sensing instrument is adapted to be successively connected in a guided manner to the object for free rotation about two non-parallel, defined axes of rotation. The sensing instrument can be rotated about these axes of rotation, and the orientation and the position of the two defined axes of rotation in space and hence the orientation and the position of the object in space can be calculated from the resulting movement of the marking element during this rotation.

10 Claims, 2 Drawing Sheets

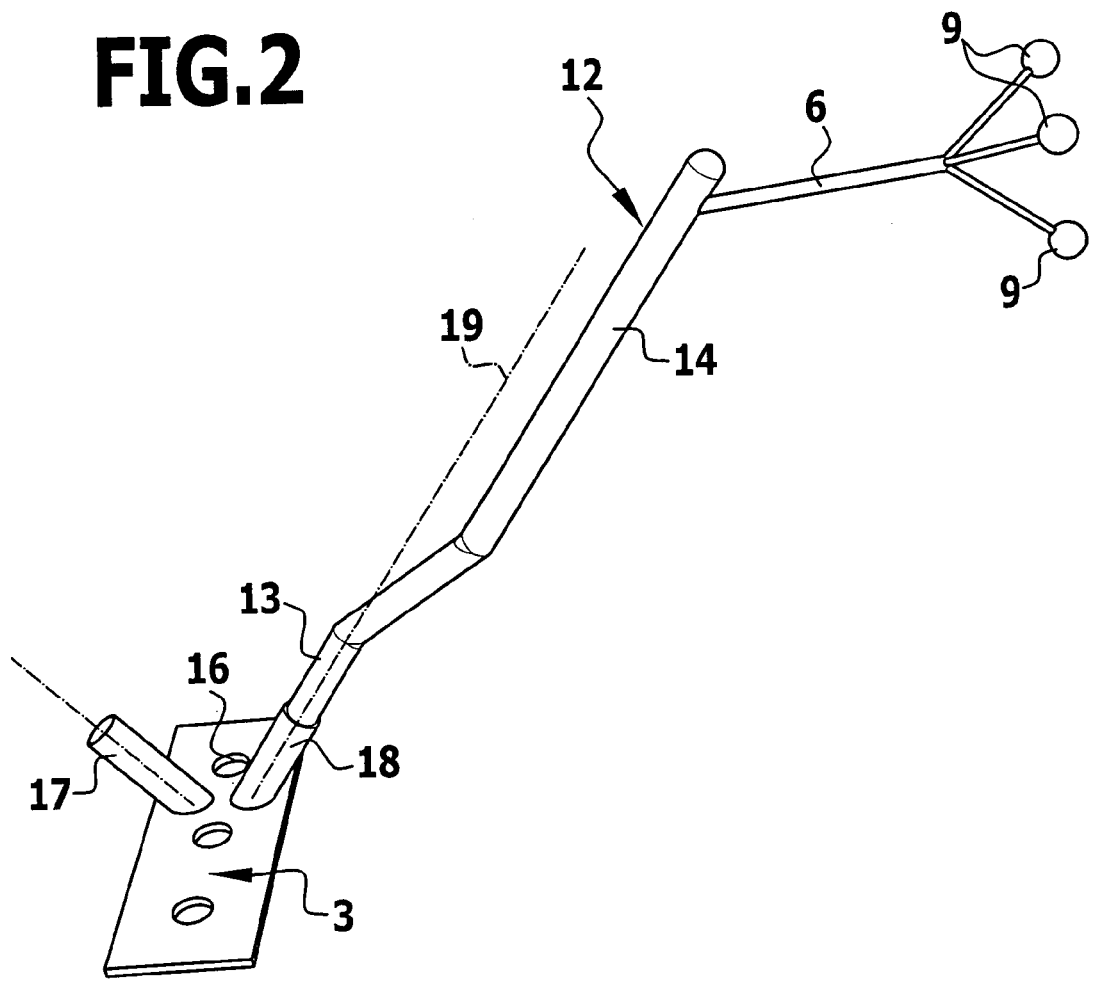

METHOD AND APPARATUS FOR DETERMINING THE POSITION OF AN OBJECT

The present disclosure relates to the subject matter disclosed in German application No. 10 2005 047 895.6 of Oct. 6, 2005, which is incorporated herein by reference in its entirety and for all purposes.

BACKGROUND OF THE INVENTION

The invention relates to a method for determining the orientation and the position of an object, in particular, a body implant, in space, with the assistance of a sensing instrument provided with a marking element and thereby determinable with respect to its orientation and its position by means of a navigation system.

Navigation systems for detecting the position of special marking elements in space are known. This position, i.e., the position in space and the orientation in space, may be determined in various ways. For example, the marking elements may have several spatially separate radiation sources or reflectors which direct radiation onto several likewise spatially separate radiation receivers, so that the position of the marking elements may be determined on the basis of the different propagation times and/or on the basis of the different orientation of the direction of emission. There are quite a large number of such navigation systems with different working mechanisms which can all be used for this purpose. The marking elements are normally directly rigidly connected to objects whose position in space is to be determined.

However, this is not possible in all cases, for example, in the case of body implants which have to be inserted through narrow openings into the body. In the case of such implants and also other objects whose position is to be determined, this determining of the position can also be carried out with the assistance of sensing instruments which are rigidly connected to a marking element whose position can be detected by the navigation system. These sensing instruments can be applied in a certain way to the objects so that the position of the object can thereby be determined, for example, by point-by-point scanning.

It is also known to make defined, in particular, conical recesses on objects for insertion of the sensing instrument therein with a sensing tip. The lowermost point of such a recess can be determined with respect to its position by moving the sensing instrument on a cone, and the position of the object in space can then also be determined from several such recesses on an object. However, this method requires the recesses to be freely accessible for a sensing instrument and, in particular, for the sensing instrument to be able to be moved freely for movement within a cone in the recess. Therefore, this possibility must also be ruled out when the objects are only accessible to a limited extent, for example, when implants are implanted inside the body.

In principle, it would also be possible to join these implants to a marking element by way of an extension and to thereby determine the position of the implant. As a rule, however, the distance between the implant and the marking element is relatively large since the implant is inserted inside the body and the marking element must be arranged outside the body. There is, therefore, the danger that the extension or connection fixing the marking element to the object will undergo deformation, which will result in erroneous measurements. Even a slight bend in such an extension can result in deviations of several degrees in the determining of the orientation.

The object underlying the invention is to so configure a method of the kind described at the outset that the position of an object can be precisely and simply determined without having to establish a rigid connection between marking element and object and without free accessibility to the object from all sides being required.

SUMMARY OF THE INVENTION

This object is accomplished in a method of the kind described at the outset, in accordance with the invention, in that the sensing instrument is successively connected in a guided manner to the object for free rotation about two non-parallel, defined axes of rotation, the sensing instrument is rotated about these axes of rotation, and the orientation and the position of the two defined axes of rotation in space and hence the orientation and the position of the object in space are calculated from the resulting movement of the marking element during this rotation.

With this method, a sensing instrument can be used which, if required, may have quite a large length, and where it does not depend on the geometrical data of the sensing instrument being known, for example, the position of a sensing tip relative to the marking element. It is merely essential that the sensing instrument be connectable to the object for free rotation about a defined axis of rotation, and that the sensing instrument be inherently rigid during the rotation about this axis of rotation, i.e., that it not undergo any uncontrolled deformation during the rotation. During rotation about the axis of rotation, the marking element then moves on a path which is concentric in relation to the axis of rotation, and the position of the axis of rotation can then be calculated from the corresponding path data, i.e., the navigation system can determine the orientation and the position of the axes of rotation in space.

These axes of rotation are characteristic of the object whose position is to be determined and thus also allow the position of the object in space to be determined.

In accordance with a first preferred embodiment, it can be provided that the two axes of rotation intersect. In this case, it is not yet possible to clearly determine the orientation of the object in space solely by determining the position of the two axes of rotation since two possible orientations result for the object when axes of rotation intersect. Therefore, in accordance with a further development of the invention, it is provided that a further position parameter of the object is determined in order to clearly determine the orientation of the object. This position parameter can be chosen in very different ways. For example, it would be possible to attach a further marking element to the object by way of an extension and to determine its position in space. The determination of this position need not be exact. A rough determination of the position is adequate here, and, therefore, errors due to deformations in the extension could also be readily tolerated. It need only be determined in which of two possible positions the object is located. It is, for example, sufficient to determine that a marking element connected to the object is located either above the plane or below the plane that is opened up by the two axes of rotation.

In another method for determining a further position parameter, a prominent point on the object, for example, a bore or an asymmetrical extension of the object, can, for example, be localized by an X-ray picture, and this may be adequate to indicate to the operator, in the case of an implant, which of two possible positions the object assumes.

In another preferred embodiment of the invention, it is provided that the two axes of rotation do not intersect. In this case, a complete determination of the position of the object is possible by determining the axes of rotation running along skew lines, without any further position parameters having to be determined.

To make a freely rotatable and guided connection, it is expedient to insert a bearing tip of the sensing instrument in a defined manner into a bore or into a bearing sleeve of the object. The operator can then carry out the determination of the position in an extremely simple way by introducing the bearing tip into the bore or into the bearing sleeve, rotating the sensing instrument in this rotary bearing and thereby determining the respective axis of rotation. This is carried out successively for the two axes of rotation.

The invention also relates to an apparatus for determining the orientation and the position of an object, in particular, a body implant, in space, comprising a sensing instrument carrying a marking element, a navigation system determining the orientation and the position of the marking element in space, and a data processor.

To determine the position of an object with such an apparatus, it is proposed, in accordance with the invention, that the data processor be programmed to calculate the orientation and the position of the two axes of rotation and hence the orientation and the position of the object in space from the position data of the marking element, which, when the sensing instrument is connected in a guided manner to the object for free rotation about two non-parallel axes of rotation, result from a rotation of the sensing instrument about these axes of rotation. As explained hereinabove, with this apparatus the axes of rotation can either intersect or extend along skew lines in relation to one another so as not to intersect.

It is expedient for the sensing instrument to have a bearing tip and for the object to have two non-parallel bores or bearing sleeves for receiving and mounting the bearing tip in a defined manner.

The invention also relates to an implant. To enable the position of such an implant in space to be determined, the implant has two non-parallel bores or bearing sleeves for mounting in a freely rotatable manner a navigatable sensing instrument, which is insertable in a respective bore or bearing sleeve for rotation about an axis of rotation defined by the longitudinal axis of the bore or the bearing sleeve. In this case, too, the axes of rotation can either intersect or follow a skew course.

The following description of preferred embodiments of the invention serves in conjunction with the appended drawings to explain the invention in further detail.

BRIEF DESCRIPTION OF THE DRAWINGS

FIG. 2 shows a bone plate with two bearing sleeves for a navigated sensing instrument.

DETAILED DESCRIPTION OF THE INVENTION

Figure 1:
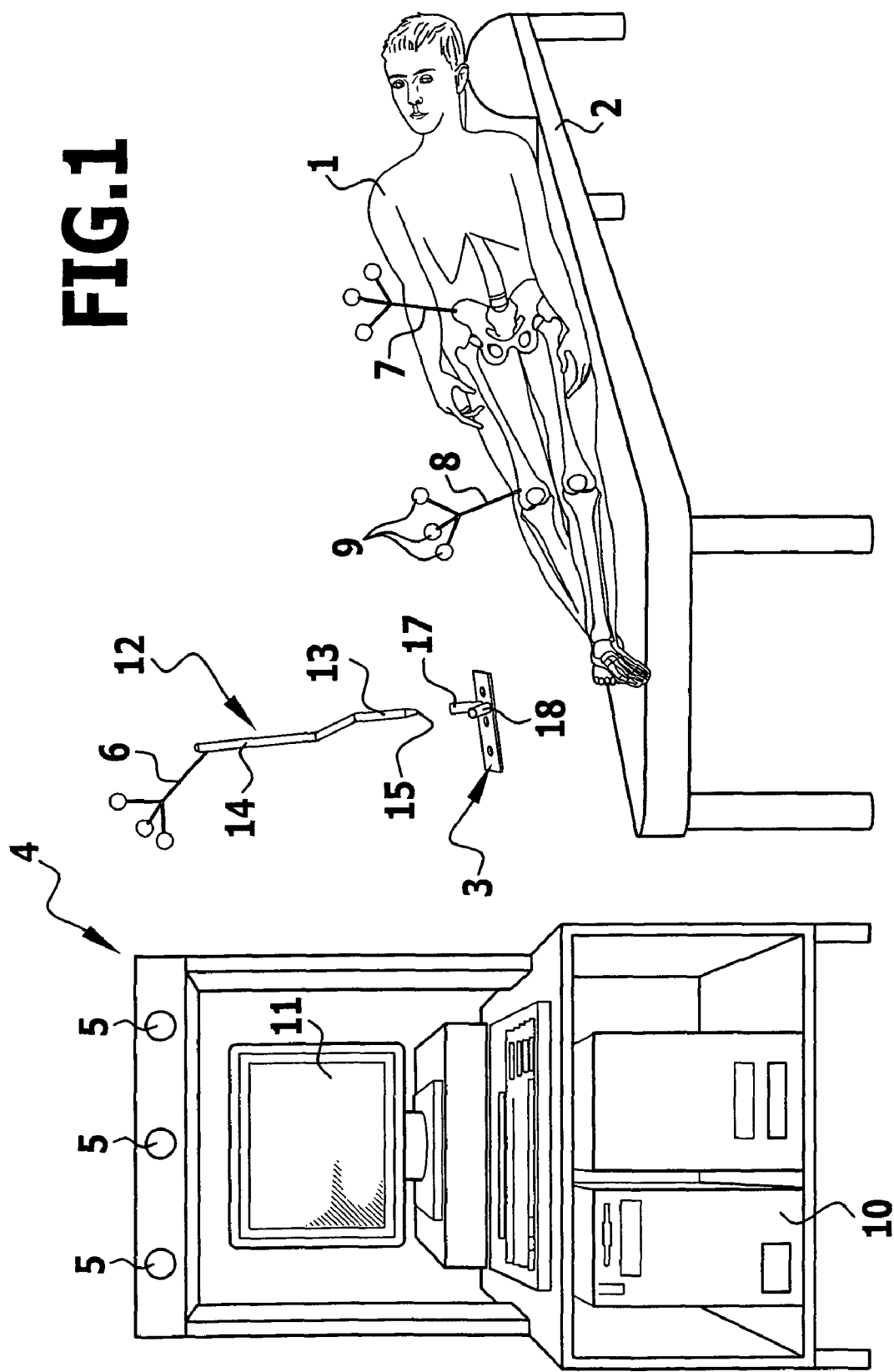
FIG. 1 shows a perspective view of a patient lying on an operating table with a navigation system for determining the position of body parts and objects.

The invention will be explained hereinbelow with reference to the determining of the position of an implant, by way of example, but it will be understood that the position of any kind of object, for example, also surgical instruments and appliances, can be detected with the method described herein.

FIG. 1 shows a patient 1 lying on an operating table 2, into whom an implant, for example, a bone plate 3, is to be inserted. There is also arranged in the operating theater in which the patient 1 is located a navigation system 4, which comprises several emitting and receiving devices 5 arranged in spaced relation to one another and marking elements 6, 7, 8, which each carry several reflection elements 9 arranged in spaced relation to one another. The reflection elements 9 reflect the electromagnetic radiation emitted by the emitting and receiving devices 5, for example, infrared radiation, and the navigation system 4 can determine from the propagation time of the radiation and, possibly, from the direction from which the reflected radiation impinges on the emitting and receiving device 5, the position and the orientation of each marking element 6, 7, 8 in space. The given position data for each marking element are fed by the navigation system 4 to a data processor 10 having an associated display device 11, for example, a conventional screen.

The marking elements can be attached to the objects and/or body parts whose position is to be determined. For example, the marking elements 7, 8 can be fixed to the pelvic bone and to the femur, respectively, of a patient. This can be carried out with the assistance of bone screws which are screwed into the bone and to which the marking elements are rigidly attached. The marking element 6 is rigidly attached to a sensing instrument 12. This sensing instrument 12 may, for example, be a simple rod which, in the illustrated embodiment, is bent at an angle, so that a front portion 13 is laterally offset from the rear portion 14. In this sensing instrument 12, the front portion 13 forms at the free end thereof a bearing tip 15. This is the foremost part of the front portion 13, which is of circular-cylindrical design.

The bone plate 3, shown as example of an implant in the drawings, has a plurality of bores 16 for receiving bone screws and also carries two circular-cylindrical bearing sleeves or guide sleeves 17, 18, which project from the plate-shaped main body of the bone plate 3, and the longitudinal axes of which are inclined in relation to one another. The bearing sleeves or guide sleeves can be arranged so that their longitudinal axes intersect. It is, however, also possible for the arrangement to be so configured that the longitudinal axes do not intersect, i.e., that these run along skew lines in relation to one another.

Both guide sleeves 17, 18 are of such dimensions that upon introducing the bearing tip 15 of the sensing instrument 12 into the guide sleeves 17, 18, which are open at their free end, the bearing tip 15 engages the guide sleeves 17, 18 with positive locking and is, therefore, mounted so as to be freely rotatable, but untiltable in the respective guide sleeve 17, 18. The sensing instrument 12 can thus be freely rotated in each guide sleeve 17, 18 about the longitudinal axis of this guide sleeve. The guide sleeve thereby forms an axis of rotation 19 for the sensing instrument 12.

In order to determine the position of the bone plate 3 in space, the sensing instrument 12 is successively inserted with the bearing tip 15 into the two guide sleeves 17, 18 and rotated, preferably through a full rotation, about the axis of rotation 19 defined by the respective guide sleeve 17, 18. During this, the marking element 6, which is rigidly connected to the sensing instrument 12, moves on a circular path arranged concentrically in relation to the axis of rotation. This applies to each individual reflection element 9 of the marking element 6. The navigation system 4 collects the position data of the marking element 6 during the entire rotational movement and feeds these position data to the data processor 10. From the position data corresponding to the movement of the marking element on the circular path, the data processor 10 can determine the orientation and the position of the axis of rotation 19 in space.

When the position and orientation data of the two axes of rotation 19 for the two guide sleeves 17, 18 are determined in this way, it is thus also possible to determine the position data of the bone plate 3.

The prerequisite therefor is merely that the data processor 10 be fed the geometrical data of the bone plate 3, in particular, the orientation of the guide sleeves 17, 18 on the bone plate 3.

If the axes of rotation 19 do not intersect, a clear determination of the position data of the bone plate results from the determination of the position data. If, on the other hand, the axes of rotation 19 intersect, there are two possible orientations for the bone plate, which result from such a relative orientation of two axes of rotation. In order to establish a clear correlation here, a further position parameter must be determined. This may be carried out visually or by means of a further marking element connected to the bone plate 3, possibly also by an X-ray picture or the like.

The sensing instrument 12 may be removable, so that the sensing instrument will not interfere with the operator at the operating site. The requirements to be met by the sensing instrument 12 are very low. It has merely to be rigid enough so as not to change its shape during the rotation. It is, however, not necessary for the sensing instrument to be calibrated in itself, i.e., for the data processor to acquire data on the geometrical shape of the sensing instrument. It is merely essential that by means of the sensing instrument a rotation of the marking element 6, connected to the sensing instrument, about the axis of rotation be possible in reproducible form.

Since the sensing instrument only rotates within itself in the proximity of the bone plate during this rotation, no space whatever is required laterally of the guide sleeves to carry out the determination of the axes of rotation, it being sufficient for access to the bone plate to remain free in the longitudinal direction of the two guide sleeves 17 and 18. This is particularly advantageous in the case of low-lying operating sites.

In the illustrated embodiment of the bone plate 3, the sensing instrument is guided by guide sleeves placed on the bone plate. In objects of a different kind, this rotary guidance could be implemented by bores in the object or by differently configured rotary couplings which permit free rotatability of the sensing instrument in relation to the object. For example, the sensing instrument could carry in the area of the bearing tip an outer thread which is screwed into a bore of the object having a corresponding inner thread. In this case, upon rotation of the sensing instrument, the marking element would describe a helical movement, and, in the same way as in the case of movement on a circular path, the data processor can calculate the orientation and the position of the axis of rotation from the corresponding path of movement.

The invention claimed is:

1. Method for determining an orientation and a position of an object, in space, comprising:

providing a sensing instrument with a marking element such that an orientation and a position of the sensing instrument is determinable by means of a navigation system, successively connecting the sensing instrument in a guided manner to the object for free rotation about each of two non-parallel, defined axes of rotation, rotating the sensing instrument about each of the two axes of rotation, calculating an orientation and a position of each of the two defined axes of rotation in space from resulting movement of the marking element during rotation about each of the two axes of rotation, and determining the position and orientation of the object in space from the calculated orientation and position of the two axes of rotation.

2. Method in accordance with claim 1, wherein the two axes of rotation intersect.

3. Method in accordance with claim 2, wherein a further position parameter of the object is determined.

4. Method in accordance with claim 1, wherein the two axes of rotation do not intersect.

5. Method in accordance with claim 1, wherein in order to establish a freely rotatable and guided connection, a bearing tip of the sensing instrument is inserted in a defined manner into one of a bore or a bearing sleeve of the object.

6. Apparatus for determining an orientation and a position of an object in space, comprising:

a sensing instrument carrying a marking element, the sensing instrument adapted to be successively connected in a guided manner to the object for free rotation about each of two non-parallel axes of rotation, a navigation system for determining an orientation and a position of the marking element in space, and a data processor, said data processor being programmed:
to calculate an orientation and a position of the two axes of rotation in space from position data of the marking element resulting from a rotation of the sensing instrument about each of the two axes of rotation; and
to determine the position and orientation of the object in space from the calculated orientation and position of the two axes of rotation.

7. Apparatus in accordance with claim 6, wherein the two axes of rotation intersect.

8. Apparatus in accordance with claim 6, wherein the two axes of rotation do not intersect.

9. Apparatus in accordance with claim 8, wherein the sensing instrument has a bearing tip, and the object has two non-parallel bores or bearing sleeves for receiving and mounting the bearing tip in a defined manner.

10. Apparatus in accordance with claim 6, wherein the sensing instrument has a bearing tip, and the object has two non-parallel bores or bearing sleeves for receiving and mounting the bearing tip in a defined manner.

* * * * *